US012576177B2

(12) United States Patent
Dycher et al.

(10) Patent No.: US 12,576,177 B2
(45) Date of Patent: Mar. 17, 2026

(54) DEVICE AND METHOD FOR EVAPORATING VOLATILE SUBSTANCES, ESPECIALLY PERFUMES AND/OR INSECTICIDES, AND HEATING BODY

(71) Applicant: CTR, LDA, Samora Correia (PT)

(72) Inventors: David Dycher, Isle of Man (GB);
Pedro Queiroz Vieira, Belas (PT)

(73) Assignee: CTR, LDA, Samora Correia (PT)

( * ) Notice: Subject to any disclaimer, the term of this
patent is extended or adjusted under 35
U.S.C. 154(b) by 1312 days.

(21) Appl. No.: 17/413,647

(22) PCT Filed: Dec. 14, 2018

(86) PCT No.: PCT/EP2018/085019

§ 371 (c)(1),
(2) Date: Jun. 14, 2021

(87) PCT Pub. No.: WO2020/119926

PCT Pub. Date: Jun. 18, 2020

(65) Prior Publication Data

US 2022/0072180 A1     Mar. 10, 2022

(51) Int. Cl.
A61L 9/03          (2006.01)
A01M 1/20          (2006.01)
(52) U.S. Cl.
CPC ........... A61L 9/037 (2013.01); A01M 1/2077
(2013.01); *A61L 2209/135* (2013.01)
(58) Field of Classification Search
CPC ...................................................... A61L 9/037
See application file for complete search history.

(56) References Cited

U.S. PATENT DOCUMENTS

| | | | |
|---|---|---|---|
| 6,446,583 B2 | 9/2002 | Vieira | |
| 2005/0185392 A1* | 8/2005 | Walter | ............... B05B 17/0684 |
| | | | 362/96 |
| 2008/0226269 A1 | 9/2008 | DeWitt et al. | |
| 2014/0037273 A1* | 2/2014 | Jaworski | ................ A61L 9/037 |
| | | | 392/390 |

(Continued)

FOREIGN PATENT DOCUMENTS

| | | |
|---|---|---|
| EP | 1108358 A1 | 6/2001 |
| EP | 0942648 B1 | 1/2002 |

(Continued)

*Primary Examiner* — Donald R Spamer
(74) *Attorney, Agent, or Firm* — Laurence A. Greenberg;
Werner H. Stemer; Ralph E. Locher

(57)          ABSTRACT

Volatile substances are evaporated from a substance container via wick inserted into the container. A wick end region protrudes from the container. A heating device has a heating body with a wick recess, forming an air flow channel with an inlet and outlet opening. The wick end region can be received under air flow around it with a circumferential gap spacing from the wick recess wall region. A penetration depth of the wick end region into the wick recess is adjustable. The wick recess has a throttling segment with a reduced flow cross section, situated above the wick end region when the wick end region protrudes into the wick recess. The position of a free wick end is adjustable relative to the throttling segment to adjust the air mass flow through the wick recess and/or the flow velocity of the substance-laden substance air flow.

25 Claims, 4 Drawing Sheets

(56)         References Cited

U.S. PATENT DOCUMENTS

2014/0124597  A1*    5/2014   Gordon ..................... A61L 9/03
                                                             239/289

FOREIGN PATENT DOCUMENTS

| | | | |
|---|---|---|---|
| EP | 2727609 | A1 | 5/2014 |
| WO | 2005106344 | A2 | 11/2005 |
| WO | 2006012249 | A2 | 2/2006 |
| WO | 2014025720 | A1 | 2/2014 |
| WO | 2019024982 | A1 | 2/2019 |

* cited by examiner

DEVICE AND METHOD FOR EVAPORATING VOLATILE SUBSTANCES, ESPECIALLY PERFUMES AND/OR INSECTICIDES, AND HEATING BODY

BACKGROUND OF THE INVENTION

Field of the Invention

The invention relates to a device for the evaporation of volatile substances, especially perfumes and/or insecticides. The device has a container, in which a substance to be evaporated is receivable, a wick inserted into the container as capillary element, protruding by a wick end region from the container, a heating device, having a heating body with a wick recess, forming an air flow channel with an inlet opening and an outlet opening spaced apart from it, and in which the wick end region can be received under air flow around it with a circumferential gap spacing from the wick recess wall region, and an adjusting device, by means of which the depth of penetration of the wick end region into the wick recess is adjustable, especially for adjusting the quantity of heat surrendered to the wick end region and/or for adjusting the quantity of substance dispensed to an air flow through the wick recess and around the wick end region to form a warm substance air flow laden with substance. Moreover, the invention relates to a heating body with a wick recess, which forms an air flow channel with an inlet opening and an outlet opening spaced apart from it and which is formed to receive in a surrounding air flow a wick end region protruding into the wick recess of a container provided with a wick, in which a substance being evaporated can be received, with a circumferential gap spacing from the wick recess wall region. The invention further relates to a method for the evaporation of volatile substances, especially perfumes and/or insecticides.

Such devices and methods for evaporation are generally known, for example from EP 1 108 358 A1. There, a device is disclosed for the evaporation of volatile substances with a housing, comprising a heating appliance. Moreover, a container for a substance being evaporated is provided, which can be connected to the housing, having a wick which is coordinated with the heating appliance by a wick end protruding from the container, the heating appliance being able to move relative to the wick end and thus the housing in order to adjust the degree of evaporation when the container is connected to the housing. Specifically, this is done in such a way that the heating appliance is fashioned as a linear guidance device mounted on the housing and able to move longitudinally relative to it, able to be fixed in different positions from the wick end to adjust the degree of evaporation. The heating appliance comprises a ceramic block as the heating body, which is provided with a continuous hole forming a wick recess. This wick recess is fashioned as a straight continuous hole with a cylindrical wick recess wall region, in which one wick end protrudes to a different degree, depending on the displacement position of the heating appliance, as is shown in FIGS. 4a and 4b:

In the displacement position of the heating body 100 represented in FIG. 4a, the arrangement is disposed in a position in which the wick end 101 has a maximum depth of penetration in the wick recess 102. In the position shown in FIG. 4b, the wick end 101 on the other hand has a significantly smaller depth of penetration in the wick recess 102, which may correspond for example to a minimum depth of penetration. Upon warming the heating body 100 by means of an electric heating element 103, not further shown here, a greater quantity of heat is put out to the wick end in the position shown in FIG. 4a than in the position shown in FIG. 4b, so that an air flow 104 through the wick recess and around the wick end is laden with more substance than in the position of FIG. 4b.

In such an embodiment of the device, a different "plume height" results in all the different positions which are represented here schematically only by FIGS. 4a and 4b as examples. The lower the plume height the higher the risk that the evaporated substance will condense in and/or on the device. Therefore, conventional heater and device designs, especially together with low or minimum depth of wick penetration (i.e. in their lower or minimum positions) bear the risk of unwanted condensation.

SUMMARY OF THE INVENTION

Therefore the problem which the present invention proposes to solve is to provide a device and a method for the evaporation of volatile substances, especially perfumes and/or insecticides, by means of which a condensation in and/or on the device can be prevented for the most diverse depths of penetration of a wick end region in a wick recess and thus for different degrees of evaporation. Another problem of the present invention is to provide a corresponding heating body.

This problem is solved with the features of the independent patent claims. Advantageous embodiments are subject matter of the dependent claims referred back to the former.

As claimed, a device is proposed for the evaporation of volatile substances, especially perfumes and/or insecticides, with a container, in which a substance being evaporated can be received, such as a liquid or the like, with a wick inserted into the container as capillary element, protruding by a wick end region from the container. Furthermore, a heating device is proposed, having a heating body with a wick recess, forming an air flow channel with an inlet opening and an outlet opening spaced apart from it, and in which the wick end region can be received under air flow around it with a circumferential gap spacing from the wick recess wall region. Moreover, an adjusting device is proposed, by means of which the depth of penetration of the wick end region into the wick recess can be adjusted, especially for adjusting the quantity of heat surrendered to the wick end region and/or for adjusting the quantity of substance dispensed to an air flow through the wick recess and around the wick end region to form a warm substance air flow laden with substance.

According to the invention, it is provided that the wick recess has a throttling segment with a reduced flow cross section, situated above the wick end region looking in the flow direction when the wick end region protrudes into the wick recess. This main aspect of the inventive idea offers a lot of advantages which will be addressed below by example and together with some other helpful definitions and explanations:

With a configuration according to the invention, the adjusting device can be used to change not only the depth of penetration of the wick end region into the wick recess, but also the position of a free wick end of the wick end region relative to the throttling segment, preferably relative to the region of the narrowest flow cross section of the throttling segment associated with the free wick end, especially in order to adjust the air mass flow through the wick recess and/or, as a key aspect, to adjust the flow velocity of the substance-laden substance air flow emerging from the outlet opening.

In this way it is achieved, as experiments by the inventors have shown, that regardless of the depth of penetration of the wick end region in the wick recess a stable performance of the device is achieved in terms of plume height and substance output into the room, without any unwanted condensation of the evaporated substance. The inventors believe, without being bound to this theory, that this is due to the fact that the throttling segment provides a throttling which influences or regulates the air flow in the region upstream from or above the wick end region, making it possible to reduce the plume diameter and increase the flow velocity of the substance air flow laden with substance in order to achieve a tall plume height regardless of the depth of penetration of the wick end region. This helps to prevent condensation.

The term "reduced flow cross section" means in particular that the throttling segment has a smaller flow cross section compared to an upstream region of the wick recess, especially a smaller flow cross section compared to an upstream situated inlet cross section of the inlet opening.

According to an especially preferred embodiment it is provided that the wick end region and thus the free wick end in a maximum position set by means of the adjusting device has the greatest depth of penetration in the wick recess and in a minimum position the least penetration in the wick recess or even no depth of penetration in the wick recess (although it is preferred that the wick has also in the minimum position at least some penetration in the wick recess). In this way, it is advantageously achieved that the free wick end in the maximum position can be supplied by the heating body with a greater quantity of heat, given the same heating power of the heating body, than in the minimum position and accordingly, given the same heating power of the heating body, a larger quantity of substance in the maximum position is put out to the air flow around and along the wick end region in the direction of the outlet opening than in the minimum position.

Furthermore, it is provided that the free wick end in the maximum position has the shortest distance and in the minimum position the furthest distance from the throttling segment associated with the free wick end, especially from the narrowest flow cross section of the throttling segment associated with the free wick end. In this way, it is advantageously achieved that, given the same heating power of the heating body, a lesser air mass flows in the maximum position through
       the wick recess than in the minimum position,
and/or
   the wick temperature is greater in the maximum position
      than in the minimum position.

That is, as a basic rule the air mass flow through the wick recess is less in a position in which the wick end region is closer to the throttling segment, but there is a greater delivery of substance due to a higher wick temperature (causing more evaporation), which higher wick temperature effects that the substance air flow flows away from the wick recess with relatively high flow velocity. On the other hand, this means that in a position in which the wick end region is further away from the throttling segment, the air mass flow through the wick recess is higher, but there is a lower delivery of substance due to a lower wick temperature (causing less evaporation), which lower wick temperature effects that the substance air flow flows away from the wick recess with lower or relatively low flow velocity (in contrary to the above mentioned relatively high flow velocity).

Of course, according to an especially preferred embodiment, it may be provided that the adjusting device can be used to adjust at least one intermediate position, preferably a plurality of different intermediate positions, between the maximum position and the minimum position. This makes possible an especially individual adjustment and adaptation of the degree of evaporation to the particular desired conditions.

The throttling segment may basically have any suitable throttle form. However, especially preferable is an embodiment in which the throttling segment provides a smooth and even surface area, preferably together with a round cross section, especially in order to avoid turbulences, and/or an embodiment in which the throttling segment tapers conically (especially in V-shape or funnel-shape), in the cross section through the wick recess and looking in the flow direction. Alternatively or additionally, the narrowest flow cross section of the throttling segment is formed at the rearmost downstream end region of the throttling segment. With such an easily producible geometry of the throttling segment, the aforementioned benefits and results can be achieved in an especially simple and functionally secure manner. Furthermore, such throttling segment geometries can be produced with especially simple manufacturing technology.

In connection with such a conical configuration of the throttling segment a steplike tapering of the throttling segment would also be essentially possible, but this might lead to unwanted turbulence and a negative influencing of the air flow. Therefore, according to an especially preferred embodiment, it is proposed that the throttling segment tapers continuously, looking in the flow direction.

Furthermore, there are various possibilities for arranging the throttling segment in the region of the wick recess. Several preferred embodiments shall be described more closely below, without this meaning a limitation of the possibilities:

Thus, for example, according to a first especially preferred embodiment, it may be provided that the throttling segment is immediately adjacent to the inlet opening and/or forms the inlet opening. In such a configuration, the throttling segment is thus arranged immediately in the region of the inlet opening. This has the advantage that a relatively large air volume can flow across the inlet opening into the wick recess.

According to an alternative embodiment, it may be provided that the throttling segment is spaced apart from the inlet opening, looking in the flow direction, and/or adjoins a cylindrical wick recess wall region, looking in the flow direction. In this variant, the throttling segment is thus situated in any case in a region of the wick recess adjacent to the inlet opening or spaced away from it and thus closer to the outlet opening, which may be advantageous for example in connection with relatively long wick recesses. In such a variant embodiment, the cylindrical wick recess wall region may immediately adjoin the inlet opening and/or form the inlet opening.

Alternatively, however, the inlet opening may also be part of a funnel-like or conically tapering inflow segment, adjoined by the or a cylindrical wick recess wall region, which is in turn adjoined by the throttling segment. Thus, here again the particular application and usage conditions can be individually coordinated and it can be dictated where precisely the throttling segment is arranged and which air volume should flow through the inlet opening into the wick recess. Thus, there is great design flexibility in connection with such a configuration. Together with such an embodiment, but also as a general rule for all embodiments, it is preferably advantageous that the wick is near to the top surface of the heater, e.g. 2 mm below the top surface of the heater, in the maximum position. The throttling segment (another term for throttling segment would be the term "restrictor") can for example come out above the heater surface but should be minimized to maintain temperature. The longer the "funnel" the larger the temperature drop. Key is here to keep the throttling segment as hot as possible to prevent condensation. Any evaporate is reheated as the plume diameter is reduced.

The outlet opening or the flow cross section of the outlet opening may also be configured basically in different ways. Especially preferred is a configuration in which the flow cross section of the outlet opening is smaller than the diameter of the wick end region. Especially in conjunction with this configuration, that is, a configuration in which the flow cross section of the outlet opening is smaller than the diameter of the wick end region, excellent results have been achieved in terms of plume height, diffusion or delivery of substance, and thus degree of evaporation.

According to another preferred embodiment the flow cross section of the outlet opening is smaller than the flow cross section of the inlet opening and/or the flow cross section of the outlet opening corresponds roughly to the smallest flow cross section of the at least one throttling segment.

According to another especially preferred embodiment, it is provided that the throttling segment passes directly into the outlet opening and forms it, preferably in the region of its smallest flow cross section. In such a design, the warm or hot substance air flow thus flows off into the surroundings of the heating body immediately upon leaving the throttling segment, which may be the case in particular with very compact, small-sized devices and the same such heating bodies.

Especially preferred, however, is an embodiment in which the throttling segment passes into an outflow channel segment of the wick recess wall region, preferably into a cylindrical outflow channel segment of the wick recess wall region, which forms the outlet opening at its end away from the throttling segment. Such an outflow channel segment may have a different length and for example it may be very short or also somewhat longer. With such an outflow channel segment an advantageous stabilization of the outflowing substance air flow can be achieved. Of course, in this instance of an outflow channel segment it is then provided preferably that the flow cross section of the outflow channel segment, preferably at least the inlet opening of the outflow channel segment, is smaller than the diameter of the wick end region and/or smaller than the flow cross section of the inlet opening of the wick recess. Further, alternatively or additionally, it may be provided that the flow cross section of the outflow channel segment, preferably at least the flow cross section of the inlet opening of the outflow channel segment, corresponds roughly to the smallest flow cross section of the at least one throttling segment.

According to another especially preferred specific embodiment it is provided that the adjusting device can be used to change the position of the container relative to the heating body and thus the position of the free wick end relative to the throttling segment. Alternatively or also additionally, the adjusting device can be used to change the position of the heating body and thus the throttling segment relative to the free wick end. For this, for example, the adjusting device can be formed by the heating body, supported on the housing of the device and able to move in the axial longitudinal direction of the wick, preferably by means of a guide slot, wherein the heating body can be fixed in different adjustment positions on the housing, preferably such that guide arms connected directly or indirectly to the heating body are led in a slot cavity at the housing side and can be fixed in different adjustment positions. Alternatively or additionally, the adjusting device may also be formed by the container supported on the housing of the device and able to move in the axial longitudinal direction of the wick, preferably by means of a screw connection, wherein the container can be fixed on the housing in different adjustment positions.

With all of the just mentioned embodiments, an especially advantageous and functionally secure adjustment possibility is achieved by means of the adjusting device.

According to another especially preferred design embodiment, the heating body is received in the interior of a housing of the device, having an outlet opening on the housing side above the outlet opening of the wick recess, looking in the axial vertical direction, by which the substance air flow emerges into the surroundings, especially with a flow velocity adjusted by means of the adjusting device and/or with a mass or quantity adjusted by means of the adjusting device.

The heating device itself has, for the heating of the heating body, preferably for the heating of the heating body made from a ceramic material or a plastic material, in one especially preferred variant embodiment at least one heating element, preferably at least one electric heating element, which is coupled in thermally conductive manner to the heating body. The at least one heating element is preferably formed by an electrical resistance element and/or is received and/or embedded in the heating body, preferably in a region of the heating body near the wick recess. Moreover, the at least one electric heating element may be electrically connected by means of electrical lines to a connection plug, preferably to a connection plug arranged on a housing of the device.

Furthermore, alternatively or additionally, a control device may be provided, preferably a control device arranged on a housing of the device, by means of which the power supply to the electric heating element can be controlled or regulated. In the simplest case, the control device may be formed, for example, by an on/off switch, by which the power supply to the electric heating element is enabled or prevented.

Moreover, according to the invention, a heating body with a wick recess is claimed, which forms an air flow channel with an inlet opening and an outlet opening spaced apart from it and which is formed to receive in a surrounding air flow a wick end region protruding into the wick recess of a container provided with a wick, in which a substance being evaporated can be received, with a circumferential gap spacing from the wick recess wall region. According to the invention, the wick recess has a throttling segment with reduced flow cross section. In regard to the definition of "reduced flow cross section", refer to the definition given above. In connection with such a design, it is especially advantageous that the throttling segment has a lesser flow cross section compared to an upstream region of the wick recess, especially compared to an upstream inflow cross section of the inlet opening, and/or the throttling segment is designed to lie above the wick end region, looking in the flow direction, for a wick end region protruding into the wick recess.

The benefits obtained with the heating body according to the invention are identical to those already discussed above in connection with the device. Accordingly, to avoid repetition, refer to the remarks given there.

The same holds in similar fashion for the subject matter of a method claim, which claims a method for the evaporation of volatile substances, especially perfumes and/or insecticides, especially by means of a device as described above. Here as well, to avoid repetition, refer to the benefits already mentioned in connection with the device. The same holds in similar manner for the dependent claims of the method, referred back to the independent method claim.

The invention shall be explained more closely below with the aid of a drawing, in schematic and exemplary manner.

DETAILED DESCRIPTION OF THE INVENTION

Figure 1:
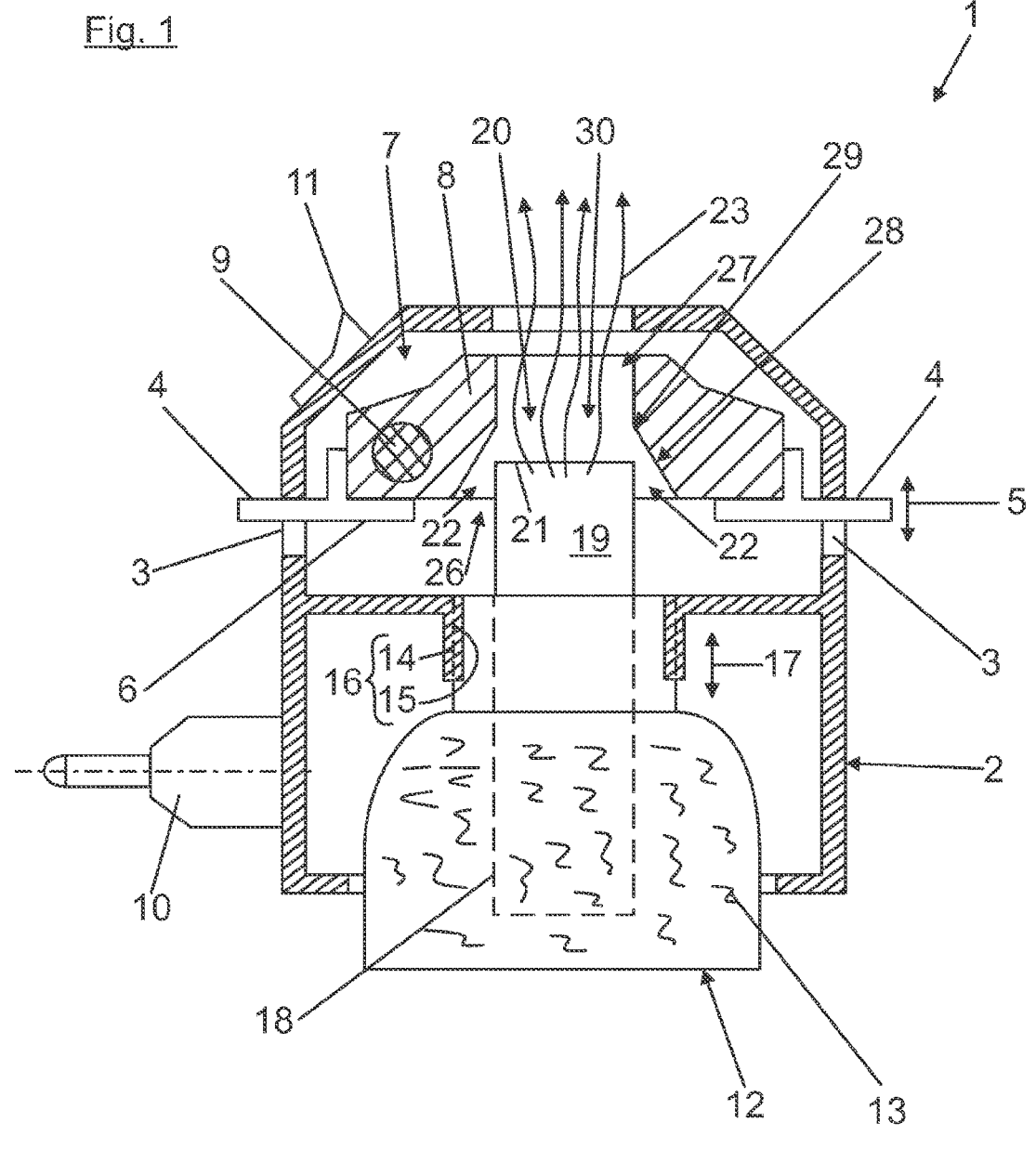
FIG. 1 schematically, a basic diagram of a cross section through an exemplary variant embodiment of a device according to the invention, FIG. 2a, 2b basic diagrams of the plume heights which can be achieved according to the invention, pertaining to different depths of penetration of a wick end region in connection with a device per FIG. 1, FIGS. 3a to 3e in schematic and exemplary manner, different variant embodiments of a heating body provided with a throttling segment in the region of the wick recess, and FIGS. 4a to 4b basic diagrams of the plume heights which can be achieved in regard to different depths of penetration of a wick end region in connection with a device according to the prior art.

FIG. 1 shows in schematic and exemplary fashion a cross section view, meant as a basic diagram, through one possible embodiment of a device 1 according to the invention for the evaporation of volatile substances, especially perfumes and/or insecticides. This device comprises a housing 2, having here oppositely situated slot cavities 3 at the housing side, in terms of the cross section, as part of a guide slot, in which guide arms 4 are led as a further component of the guide slot and can be fixed in different adjustment positions, although that is not represented here in detail. The direction of movement of the guide arms 4 in the slot cavities 3 is shown schematically by the arrow 5.

As can further be seen in FIG. 1, the guide arms 4 are part of a support element 6 of a heating device. The support element 6 here, for example, carries only one heating body 8 of the heating device 7.

The heating body 8 itself may be formed, for example, from a plastic material or a ceramic material and it comprises an electric heating element 9, such as an electrical resistance element (e.g., a PTC resistance element), which in known manner is electrically connected by electrical lines, not represented here for reasons of clarity, to a connection plug 10.

Moreover, there is shown here only very schematically a control device, represented symbolically by a switch 11, by means of which the power supply to the electrical heating element 9 can be controlled or regulated.

As is further evident from FIG. 1, a container 12 is supported on the housing 2 of the device 1, in which a substance 13 being evaporated is received.

As is shown only very schematically in FIG. 1 and represented in connection with the threaded region 14, the container 12 may optionally be supported by this threaded region 14 in height adjustable manner and thus able to be displaced in the housing. For this, the container 12 likewise has a threaded region 15, so that the two threaded regions 14, 15 form a screw connection 16, by means of which the container 12 can move in the direction of the double arrow 17 relative to the housing and thus relative to the heating body 8.

The guide slot formed from guide arms 4 and slot cavities 3 and/or the screw connection 16 thus form here an adjusting device, by means of which the position of the container 12 relative to the heating body 8 can be changed.

Moreover, a wick 18 is inserted in the container 12 as a capillary element, which protrudes by a wick end region 18 from the container 12.

As can furthermore be seen from FIG. 1, the wick end region 19 protrudes into a wick recess 20 of the heating body 8, the depth of penetration of the wick end region 19 in the wick recess 20 being changeable and adjustable by means of one or both of the two above-described adjusting devices.

The further the wick end region 19 penetrates by its free wick end 21 into the wick recess 20, the more heat is given off to the wick end region 19 and the more the air flow 22 around the wick end region 19 is enriched to form a substance-laden substance air flow 23.

As is further well shown in FIG. 1, the wick end region 19 is received in the wick recess 20 with a circumferential gap spacing 24 from the wick recess wall region 25 in a surrounding air flow. Thus, the wick recess 20 forms an air flow channel with an inlet opening 26 and an outlet opening 27 spaced apart from it, wherein the pure air flow 22 not laden with substance flows across the inlet opening 26 into the wick recess 20, becomes laden with substance there, and flows away through the outlet opening 27 as warm or hot substance-laden substance air flow 23.

Figures 2A, 2B:
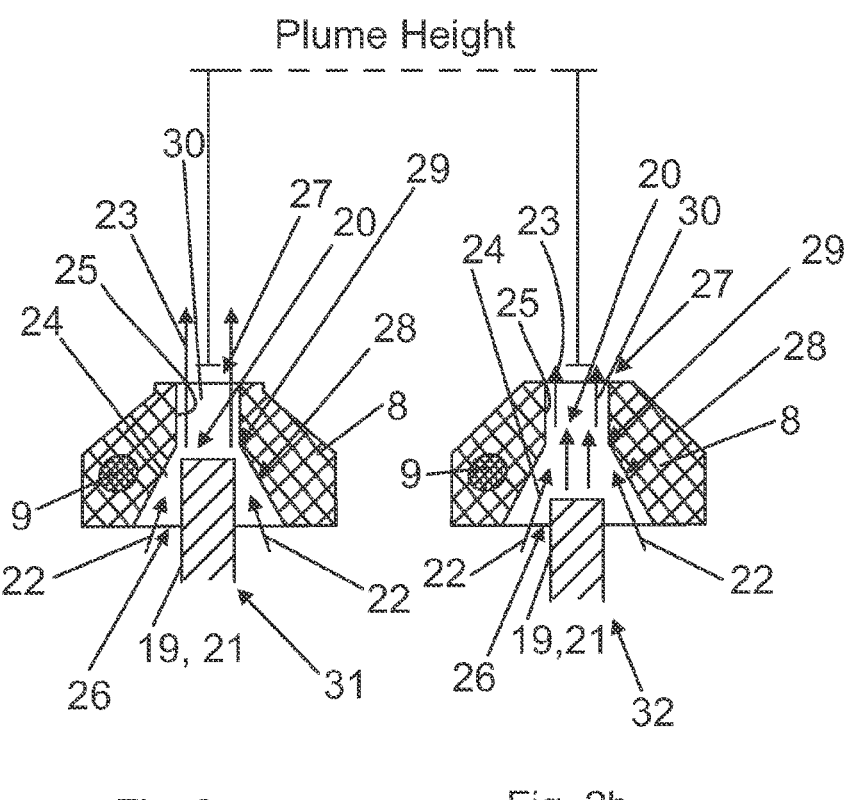

As can be seen from FIG. 1 taken together with FIGS. 2a and 2b, the wick recess 20 has a throttling segment 28 with reduced flow cross section, which lies above the wick end region 19, especially above the free wick end 21, when a wick end region 19 is protruding into the wick recess 20, looking in the flow direction.

In this way, the adjusting device when activated can also change the position of the free wick end 21 of the wick end region 19 relative to the throttling segment 28, especially relative to the region of the narrowest flow cross section of the throttling segment 28 associated with the free throttle end 21, in order to be able to adjust or change the air mass flow through the wick recess 20 or the flow velocity of the substance air flow 23 emerging from the outlet opening 27 and laden with substance.

The throttling segment 28 is conically tapered, especially V-shaped or funnel-shaped, in the cross section through the wick recess and looking in the flow direction, preferably so that the smallest or narrowest flow cross section 29 of the throttling segment 28 is formed at the rearmost downstream end region of the throttling segment 28. The throttling segment 28 tapers continuously in the exemplary embodiment shown here, looking in the flow direction.

As can further be seen from considering FIGS. 1, 2a and 2b together, the throttling segment 28 here immediately adjoins the inlet opening 26 and helps to form the latter, merely as an example.

The throttling segment 28 in this exemplary embodiment further passes into an outflow channel segment 30 with a cylindrical cross section, for example here, forming the outlet opening 27 at its end away from the throttling segment 28.

In the exemplary embodiment shown here, the flow cross section of the cylindrical outflow channel segment 30 is furthermore smaller than the flow cross section of the inlet opening 26 of the wick recess 20 and furthermore smaller than the diameter of the wick end region 19. Furthermore, the flow cross section of the outflow channel segment 30 corresponds here, merely as an example, to the smallest or least flow cross section 29 of the throttling segment 28.

By means of the adjusting device, the position of the heating body 8 relative to the container 12 and thus to the wick end region 19 can be changed so that the wick end region 19 and thus the free wick end are in a maximum position 31, represented in FIG. 2a, in which the wick end region 19 and thus the free wick end 21 have the greatest depth of penetration in the wick recess 20. In this maximum position 31, the free wick end 21 is supplied with a greater quantity of heat from the heating body 8 than in the minimum position 32, shown for example in FIG. 2b, in which the wick end region 19 and thus the free wick end 21 have a correspondingly smaller (or even no) depth of penetration in the wick recess 20. This, of course, pertains to an identical or nearly identical heating power of the heating body 8, so that in the maximum position 31 represented for example in FIG. 2a a greater quantity of substance is put out to the air flow 22 around and along the wick end region 19 in the direction of the outlet opening 27 than in the minimum position 32 represented in FIG. 2b.

Of course, the minimum position 32 represented in FIG. 2b is to be understood only schematically and as an example, and of course it may also be provided in the minimum position that the free wick end 21 has no depth of penetration at all in the wick recess 20 and accordingly it may be arranged even further below than is shown in FIG. 2b. Also the maximum position 31 shown in FIG. 2a should only be understood as an example. In this maximum position 31, of course, any particularly desired spacing from the throttling segment 28 can be provided.

As can further be seen from the schematic representations of FIGS. 2a and 2b, the free wick end 21 in the maximum position 31 has the shortest distance and in the minimum position 32 the furthest distance from the throttling segment 28 associated with the free wick end, especially from the narrowest flow cross section 29 of the throttling segment 28 associated with the free wick end 21. In this way, given the identical heating power of the heating body 8, a lesser air mass flows through the wick recess 20 in the maximum position 31 than in the minimum position 32, or given the identical heating power of the heating body 8 the flow velocity of the substance air flow 23 emerging from the outlet opening 27 in the maximum position 31 is greater than that in the minimum position 32. Furthermore, the wick end region 19 in the maximum position 31 is supplied with a greater amount of heat from the heating body 8 than in the minimum position 32, so that the substance air flow 23 in the maximum position 31 is laden with a larger amount of substance than in the minimum position 32.

Even though not explicitly shown in FIGS. 2a and 2b, it is self evident that the adjusting device can be used optionally to adjust at least one intermediate position, preferably a plurality of different intermediate positions, between the maximum position 31 and the minimum position 32.

As is shown schematically and basically in FIGS. 2a and 2b, the substance air flow 23 emerging from the device 1 and laden with substance thus has a roughly identical plume height in all wick positions (including all intermediate positions between the maximum position 31 and the minimum position 32) and the substance air flows 23 in the different wick positions thus differ only in terms of the amount of substance with which the air flow is laden.

In this way, it is possible to provide a stable and always identical or also sufficiently tall plume height, always independently of the wick position, by means of which a delivery of substance by diffusion into the room occurs in effective manner in all wick positions.

FIGS. 3a to 3e now show different embodiments of other configurations of the wick recess 20 according to the invention.

Figures 3A, 3B, 3C, 3D:
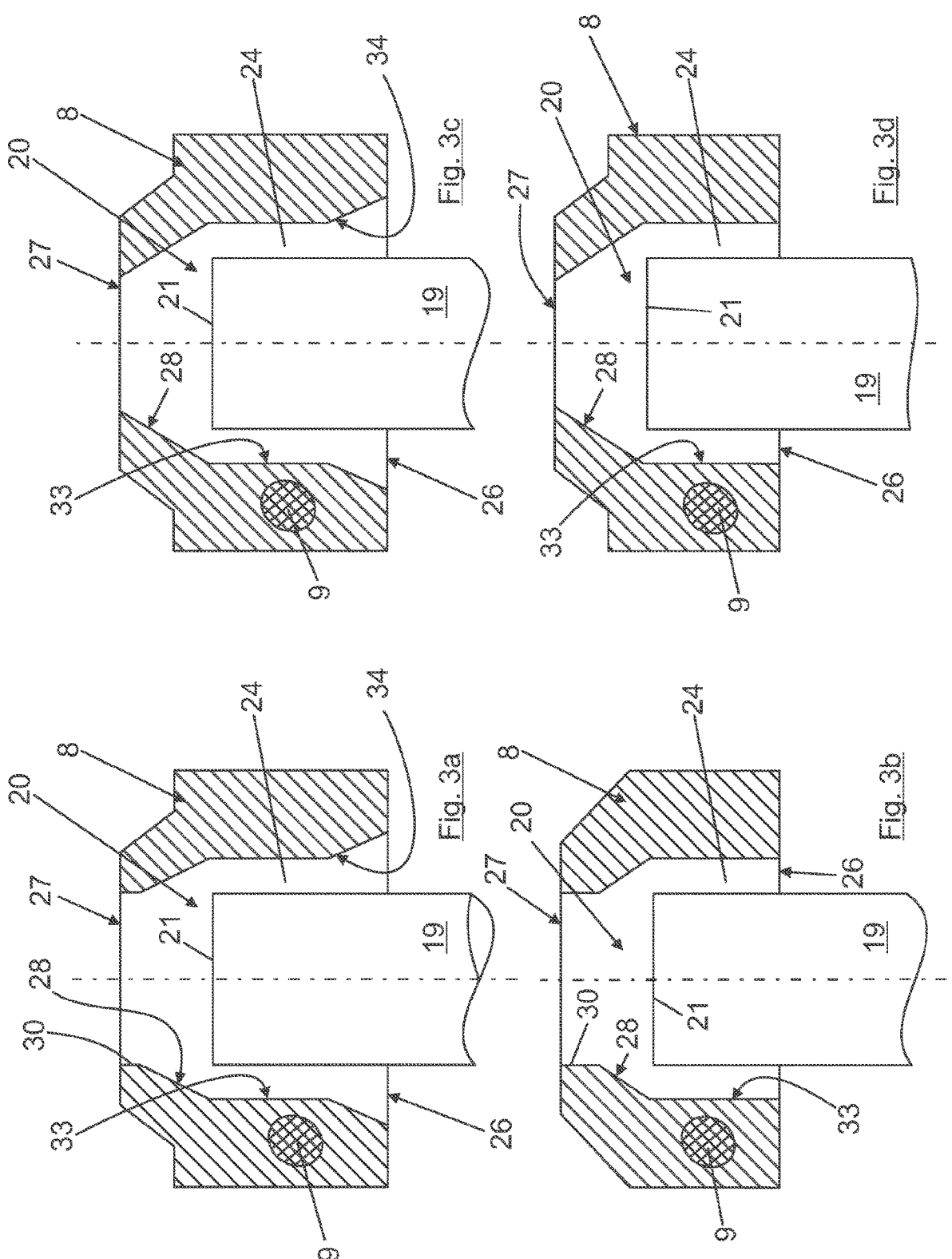

In FIG. 3a, the wick recess 20 is configured so that the throttling segment 28 is spaced away from the inlet opening 26, looking in the flow direction, and adjoins a cylindrical wick recess wall region 33, looking in the flow direction. The inlet opening 26 here is furthermore part of an inflow segment 34 which tapers conically or in funnel fashion, adjoined by the cylindrical wick recess wall region 33 and in turn being adjoined by the throttling segment 28.

Adjoining the throttling segment 28, shown here merely as an example, is a relatively short cylindrical outflow channel segment 30, which forms the outlet opening 27.

Here as well the flow cross section of the outlet opening 27 or of the outflow channel segment 30 is preferably less than the diameter of the wick end region 19 and smaller than the flow cross section of the inlet opening 26, so that once again as an example the flow cross section of the outlet opening 27 or of the outflow channel segment 30 corresponds to the smallest flow cross section of the throttling segment 28.

The configuration of FIG. 3b differs from that of FIG. 3a merely in that here no funnel-shaped or conically tapering inflow segment 34 is provided, but instead the cylindrical wick recess wall region 33 extends as a straight line downward to the inlet opening 26 and helps to form it.

FIG. 3c shows another alternative configuration, which differs from that of FIG. 3a merely in that the throttling segment 28 passes directly into the outlet opening 27 and forms this in the region of its smallest flow cross section 29, that is, no outflow channel segment is formed there. Otherwise, the configuration of FIG. 3c corresponds to that of FIG. 3a.

The configuration of FIG. 3d differs from that of FIG. 3c merely in that no funnel-shaped or conically tapering inflow segment 34 is provided there in the region of the inlet opening 26, but instead the cylindrical wick recess wall region 33 extends as a straight line downward to the inlet opening 26 and helps to form it.

Figure 3E:
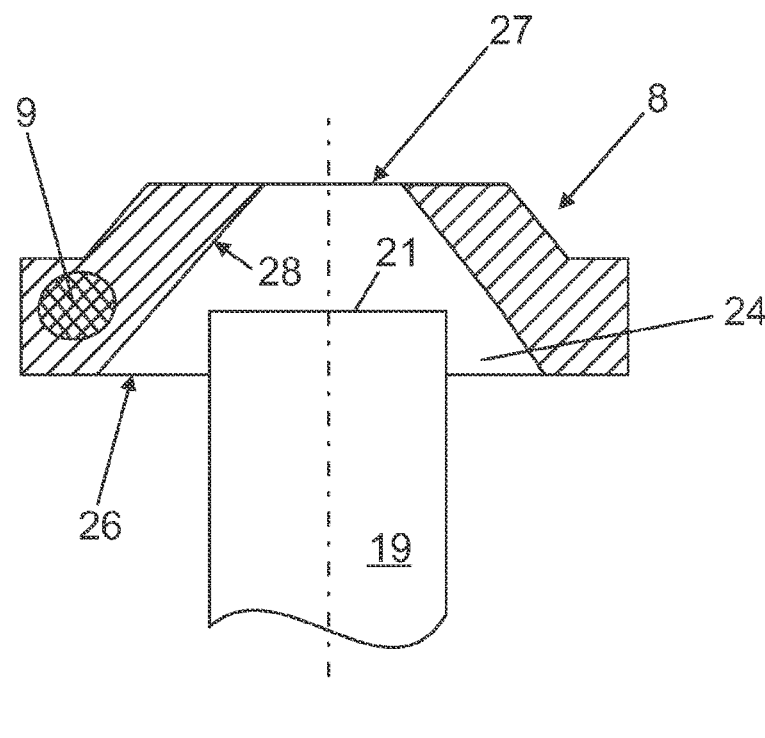
Figures 4A, 4B:
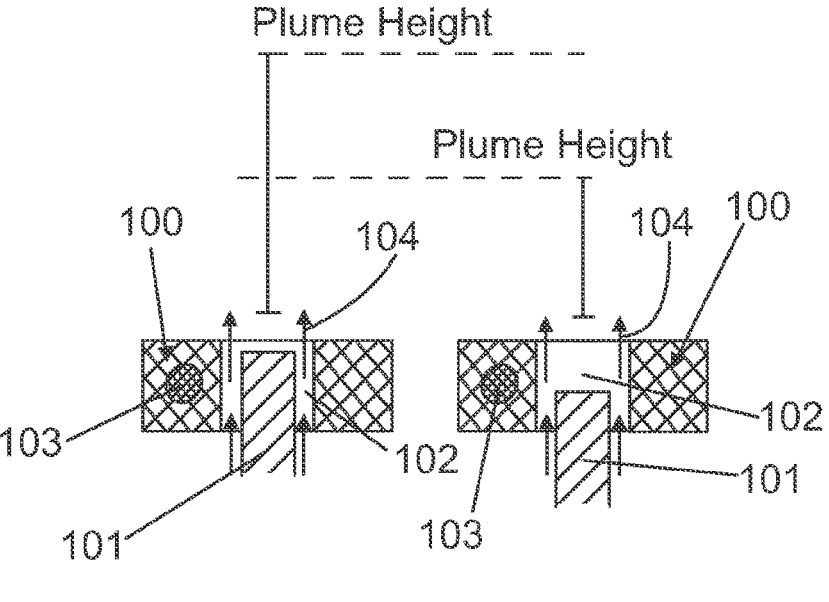

And finally FIG. 3e shows a configuration in which the entire wick recess 20 has only one throttling segment 28, forming both the inlet opening 26 and the outlet opening 27.

As can further be seen from FIG. 1, the housing has an outlet opening 35 on the housing side in the region above the outlet opening 27, looking in the vertical axial direction, by which the substance air flow 23 emerges and flows away into the surroundings 36 with a flow velocity adjusted by means of the adjusting device and with a mass or volume adjusted by means of the adjusting device.

The invention claimed is:

1. A device for evaporating volatile substances, the device comprising:

a container configured to receive a substance to be evaporated;

a wick inserted into the container to form a capillary element, said wick having a wick end region protruding from said container;

a heating device having a heating body being configured to supply heat to said wick end region, and said heating body being formed with a wick recess, forming an air flow channel with an inlet opening and an outlet opening spaced apart from said inlet opening, wherein said wick end region is receivable in said wick recess with an air flow around said wick and a circumferential gap spacing from a wall of said wick recess;

said wick recess being formed with a throttling segment having a reduced flow cross section above said wick end region in an upward flow direction when said wick end region protrudes into said wick recess; and an adjusting device configured to adjust a depth of penetration of said wick end region into said wick recess, said adjusting device being configured to change a position of a free wick end of said wick end region relative to said throttling segment, in order to adjust an air mass flow through said wick recess and/or to adjust a flow velocity of a substance-laden substance air flow emerging from said outlet opening.

2. The device according to claim 1, wherein said adjusting device is configured for adjusting the quantity of heat surrendered to said wick end region and/or for adjusting a quantity of substance dispensed to the air flow through said wick recess and around said wick end region to form a warm substance air flow laden with substance, and said adjusting device is configured to change the position of the free wick end relative to a region of a narrowest flow cross section of said throttling segment.

3. The device according to claim 1, wherein said wick end region and thus said free wick end, in a maximum position set by way of said adjusting device, has a greatest depth of penetration in said wick recess and, in a minimum position, said free wick end has the least or no depth of penetration in said wick recess, wherein said free wick end in the maximum position is supplied by said heating body with a greater quantity of heat, given an equal heating power of said heating body, than in the minimum position and, given the equal heating power of said heating body, a larger quantity of the substance is output in the maximum position than in the minimum position to the air flow around and along said wick end region in the direction of the outlet opening;

and/or said free wick end, in the maximum position, has a shortest distance and, in the minimum position, has a furthest distance from said throttling segment associated with said free wick end, and, given the same heating power of said heating body, a lesser air mass flows in the maximum position through said wick recess than in the minimum position and/or, given the same heating power of the heating body, a wick temperature is greater in the maximum position than in the minimum position.

4. The device according to claim 3, wherein said adjusting device is useable to adjust at least one intermediate position or a plurality of different intermediate positions between the maximum position and the minimum position.

5. The device according to claim 1, wherein said throttling segment has a smooth and even surface area and/or tapers conically along the flow direction in a cross section through said wick recess and/or a narrowest flow cross section of said throttling segment is formed at a rearmost downstream end region of said throttling segment.

6. The device according to claim 5, wherein said throttling segment has a round cross section or tapers in a V-shape or funnel-shape in the cross section through said wick recess.

7. The device according to claim 5, wherein said throttling segment tapers continuously along the flow direction.

8. The device according to claim 1, wherein throttling segment is immediately adjacent said inlet opening or forms said inlet opening.

9. The device according to claim 1, wherein said throttling segment is spaced apart from said inlet opening, along the flow direction, and/or adjoins a cylindrical wick recess wall region, in the flow direction.

10. The device according to claim 9, wherein said cylindrical wick recess wall region is immediately adjacent said inlet opening or forms said inlet opening.

11. The device according to claim 1, wherein said inlet opening is a part of a funnel-shaped or conically tapering inflow segment, adjoined by a cylindrical wick recess wall region, which is in turn adjoined by said throttling segment.

12. The device according to claim 1, wherein a flow cross section of said outlet opening is smaller than a diameter of said wick end region.

13. The device according to claim 1, wherein a flow cross section of said outlet opening is smaller than a flow cross section of said inlet opening or the flow cross section of said outlet opening is approximately equal to a smallest flow cross section of said throttling segment.

14. The device according to claim 1, wherein said throttling segment, along the flow direction, passes directly into said outlet opening and forms said outlet opening.

15. The device according to claim 1, wherein said throttling segment, along the flow direction, passes into an outflow channel segment of a wick recess wall region, while a flow cross section of the outflow channel segment is smaller than a flow cross section of said inlet opening of said wick recess or smaller than a diameter of said wick end region, and/or wherein the flow cross section of the outflow channel segment is substantially equal to a smallest flow cross section of said at least one throttling segment.

16. The device according to claim 1, wherein said adjusting device is configured to change a position of said container relative to said heating body and a position of said free wick end relative to said throttling segment or wherein said adjusting device is configured to change a position of said heating body and said throttling segment relative to said free wick end.

17. The device according to claim 16, wherein said adjusting device is formed by said heating body, supported on a housing of the device and is configured to move in an axial longitudinal direction of said wick, wherein said heating body is fixable in different adjustment positions on the housing, such that guide arms connected directly or indirectly to said heating body are led in a slot cavity of a guide slot at a housing side and are fixable in different adjustment positions, or wherein said adjusting device is formed by said container supported on the housing of the device and able to move in an axial longitudinal direction of the wick by way of a screw connection, which enables said container to be fixed on said housing in different adjustment positions.

18. The device according to claim 1, wherein said heating body is received in an interior of a housing of the device, having an outlet opening on a housing side above said outlet opening of said wick recess, along an axial vertical direction, by which the substance air flow emerges into surroundings, with a flow velocity, or a mass, or a quantity adjusted by way of said adjusting device.

19. The device according to claim 1, wherein said heating device includes at least one heating element for heating said heating body, said at least one heating element is coupled in thermally conductive manner to said heating body.

20. The device according to claim 19, wherein said heating body is made of a ceramic material or a plastic material, said at least one heating element is an electric heating element formed by an electrical resistance element received or embedded in said heating body in a region near said wick recess.

21. The device according to claim 20, wherein said at least one electric heating element is electrically connected by way of electrical lines to a connection plug and a control device is configured to control or closed-loop control a power supply to said electric heating element.

22. A method for evaporating volatile substances the method comprising:

providing an evaporation device with a container, in which a substance to be evaporated is received; a wick inserted into the container as capillary element, protruding by a wick end region from the container; a heating device, having a heating body being configured to supply heat to said wick end region, and said heating body being formed with a wick recess, forming an air flow channel with an inlet opening and an outlet opening spaced apart from the inlet opening, and in which the wick end region can be received under air flow around the wick with a circumferential gap spacing from the wick recess wall region; and an adjusting device, by means of which a depth of penetration of the wick end region into the wick recess and thus a quantity of heat transferred to the wick end region and/or by means of which a quantity of the substance dispensed to an air flow through the wick recess and around the wick end region is adjustable;

providing the wick recess with a throttling segment having a reduced flow cross section, situated above the wick end region looking in a flow direction when the wick end region protrudes into the wick recess; and activating the adjusting device to change, in addition to a depth of penetration of the wick end region, a position of a free wick end of the wick end region relative to the throttling segment, to change the position relative to a region of a narrowest flow cross section of the throttling segment associated with the free wick end, and thereby adjust an air mass flow through the wick recess or a flow velocity of a substance-laden substance air flow emerging from the outlet opening.

23. The method according to claim 22, which comprises:

selectively setting the wick end region and the free wick end to a maximum position wherein the free wick end has a greatest depth of penetration in the wick recess;

selectively setting the wick end region and the free wick end to a minimum position wherein the free wick end has a least penetration or no depth of penetration in the wick recess;

wherein the free wick end in the maximum position is supplied by the heating body with a greater quantity of heat, given the same heating power of the heating body, than in the minimum position and, given the same heating power of the heating body, expelling a larger quantity of the substance in the maximum position to the air flow around and along the wick end region in the direction of the outlet opening than in the minimum position;

or wherein the free wick end in the maximum position has a shortest distance and in the minimum position a greatest distance from the throttling segment associated with the free wick end, and from a narrowest flow cross section of the throttling segment associated with the free wick end, so that, given the same heating power of the heating body, a lesser air mass flows in the maximum position through the wick recess than in the minimum position or that, given the same heating power of the heating body, a wick temperature is greater in the maximum position than in the minimum position.

24. The method according to claim 23, which comprises selectively setting with the adjusting device at least one or a plurality of intermediate positions between the maximum position and the minimum position.

25. The method according to claim 22, which comprises setting a substance air flow emerging from the device that is laden with the substance to have approximately the same plume height in all wick positions and causing the substance air flow in different wick positions to differ only in terms of an amount of substance with which the substance air flow is laden.

* * * * *